United States Patent [19]

Granfors et al.

[11] Patent Number: 5,751,783
[45] Date of Patent: May 12, 1998

[54] DETECTOR FOR AUTOMATIC EXPOSURE CONTROL ON AN X-RAY IMAGING SYSTEM

[75] Inventors: Paul R. Granfors; Jean-Claude Morvan, both of Milwaukee; Rowland F. Saunders, Hartland, all of Wis.

[73] Assignee: General Electric Company, Waukesha, Wis.

[21] Appl. No.: 771,725

[22] Filed: Dec. 20, 1996

[51] Int. Cl.⁶ .................................................. H05G 1/44
[52] U.S. Cl. .................................... 378/108; 378/97
[58] Field of Search ........................... 378/108, 109, 378/110, 111, 112, 96, 97; 250/368, 370.09, 370.11

[56] References Cited

U.S. PATENT DOCUMENTS

| | | |
|---|---|---|
| 4,980,905 | 12/1990 | Meccariello ........................ 378/207 |
| 4,996,413 | 2/1991 | McDaniel et al. ................. 250/208.1 |
| 5,041,888 | 8/1991 | Possin et al. ........................ 357/23.7 |
| 5,264,701 | 11/1993 | Crain ...................................... 250/374 |
| 5,267,295 | 11/1993 | Strommer ......................... 378/108 X |
| 5,331,166 | 7/1994 | Yamamoto et al. ............... 378/97 X |
| 5,352,884 | 10/1994 | Patrick et al. .................... 250/208.1 |
| 5,401,668 | 3/1995 | Kwansnick et al. ..................... 437/3 |

*Primary Examiner*—David P. Porta
*Attorney, Agent, or Firm*—Quarles & Brady

[57] ABSTRACT

Automatic exposure control for an x-ray system using a large area solid state x-ray detector includes an array of photodiodes located behind the x-ray image detector to measure photons passing therethrough. The resulting currents from selective ones of these photodiodes are combined to provide a signal used to control the x-ray exposure.

6 Claims, 4 Drawing Sheets

DETECTOR FOR AUTOMATIC EXPOSURE CONTROL ON AN X-RAY IMAGING SYSTEM

BACKGROUND OF THE INVENTION

The field of the invention is x-ray imaging systems, and particularly, automatic exposure control for x-ray systems.

Automatic exposure control (AEC) is used in x-ray imaging equipment to control the exposure per image. The goal is to maintain image quality while minimizing patient exposure. The AEC develops a signal proportional to the x-ray flux into the image receptor. This signal is used to regulate the total exposure for each image either by terminating the exposure or by adjusting the x-ray flux rate.

There are several methods of automatic exposure control currently in use. One of these uses an ionization chamber detector placed between the patient and the imaging detector. The ion chamber detector can be composed of several separate chambers, in which case the exposure-control signal can come from any single chamber or a combination of chambers. One disadvantage of this type of detector is that some of the radiation that would otherwise contribute to signal in the image receptor is lost because of attenuation in the ion chamber. Such chambers must also be carefully constructed so that any variation in absorption over their area is small enough to preclude artifacts in the detected image.

In another AEC method an ion chamber is placed behind the image receptor. In this position it does not intercept x-rays used for imaging, but the available radiation, and thus the signal in the ion chamber, is reduced because of attenuation in the image receptor and any associated packaging or shielding. The thickness of the ion chamber could be increased to increase its sensitivity, but this would make the imaging system more bulky. Some AEC systems employ a scintillating screen coupled to a light sensor in place of the ion chamber.

Another AEC method, which is used with image intensifier based systems, collects some of the light from the image gate at the output of the image intensifier and detects the brightness level with a photosensor. A disadvantage of this AEC method is that the light-pickup device is placed in the image path. This can lead to interference of the image by the pickup device in some imaging situations.

X-ray imaging systems which employ a large area solid state x-ray detector, such as that described in U.S. Pat. No. 4,996,413 entitled "*Apparatus And Method For Reading Data from An Image Detector*", cannot use the AEC method employed in image intensifier systems. Unlike an image intensifier system, there is no minified light image from which light can be conveniently collected. Also, one of the design objectives when using large area solid state detectors is to reduce the bulk of the detector package. This makes the use of an ion chamber placed in front of or behind the image detector less desirable.

SUMMARY OF THE INVENTION

The present invention is an AEC detector containing an array of photosensors disposed behind the image detector to detect the x-rays and/or light passing therethrough. The number and location of the photosensors used for exposure control, the AEC "field of view", can be adjusted for different imaging procedures by selectively combining the photosensor signals to detect x-rays and/or light from one or more regions of the desired shape and size.

A general object of the invention is to provide an AEC signal without producing image artifacts or significantly increasing the size of the detector package. The photosensor array is disposed behind the image receptor and will not, therefore, interfere with the image formation. The photosensor array may be constructed using a number of different technologies, which result in a minimal increase in the size of the detector package.

A more specific object of the invention is to provide an AEC signal from a field of view that can be selectively adjusted. A selector circuit combines the signals from each array photosensor and the field of view can be adjusted by selecting which signals are included in the combination.

DESCRIPTION OF THE PREFERRED EMBODIMENT

Figure 1:
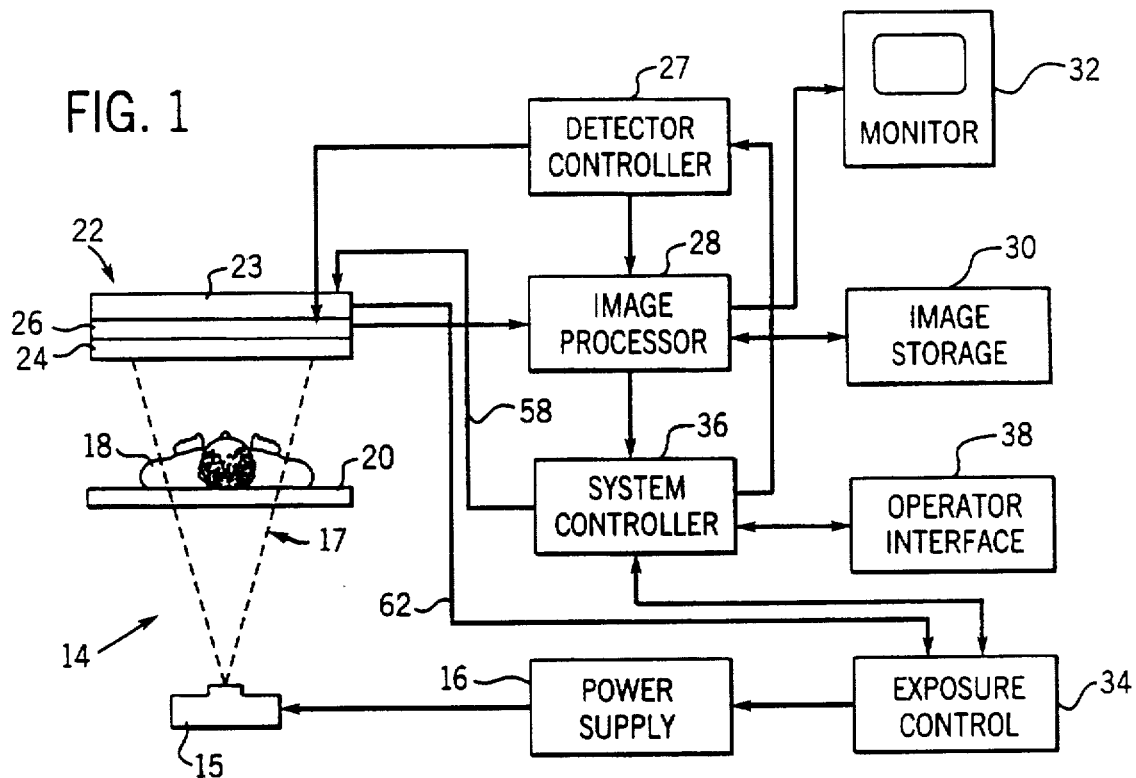
FIG. 1 is a pictorial representation of an x-ray imaging system which employs the present invention.

With initial reference to FIG. 1, an x-ray apparatus 14 includes an x-ray tube 15 which, when excited by a power supply 16, emits an x-ray beam 17. As illustrated, the x-ray beam is directed toward a patient 18 lying on an x-ray transmissive table 20. The portion of the beam which is transmitted through the table and the patient impinges upon an x-ray detector assembly 22. The x-ray detector assembly 22 comprises a scintillator 24 that converts the x-ray photons to lower energy photons in the visible spectrum. Contiguous with the scintillator 24 is an image photodetector array 26, which converts the light photons into an electrical signal. A detector controller 27 contains electronics for operating the detector array 26 to acquire an image and to read out the signal from each photodetector element.

The output signal from the image photodetector array 26 is coupled to an image processor 28 that includes circuitry for collecting, processing and enhancing the x-ray image signal. The processed image is displayed on a video monitor 32 and may be stored in an image storage device 30. The overall operation of the x-ray apparatus 14 is governed by a system controller 36 which receives commands from the user via an operator interface panel 38.

The image photodetector array 26 consists of amorphous silicon devices on a glass substrate. A portion of the light from the scintillator 24 is transmitted through these silicon devices and through the spaces between them. In addition, some of the x-rays are transmitted through both the scintillator 24 and the image photodetector array 26. An AEC photosensor array 23, disposed on the back side of the image detector array 26, detects this light and these x-rays and it produces an AEC signal which is output to an exposure control circuit 34. It is the construction and operation of this AEC photosensor array 23 which is the subject of the present invention. It will be described in more detail below.

Figure 2:
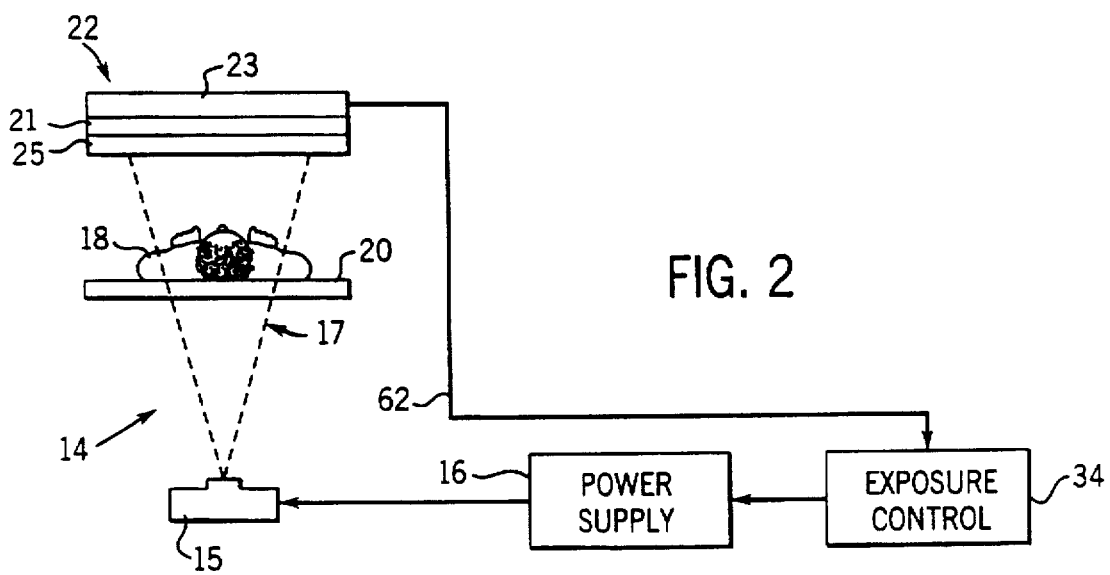
FIG. 2 is a pictorial representation of another x-ray system which employs the present invention.

The AEC photosensor array 23 of the present invention may also be used in a second preferred embodiment, illustrated in FIG. 2, in which it is used with a film/screen imaging sensor 25. In this embodiment, the AEC detector consists of a scintillator 21 coupled to a photosensor array 23. The scintillator 21 is used to absorb x-rays transmitted through the film/screen sensor 25 and produce light photons which are absorbed by the photosensors in the AEC photosensor array 23. The operation of the AEC photosensor array 23 is the same as in the first preferred embodiment.

Figure 3:
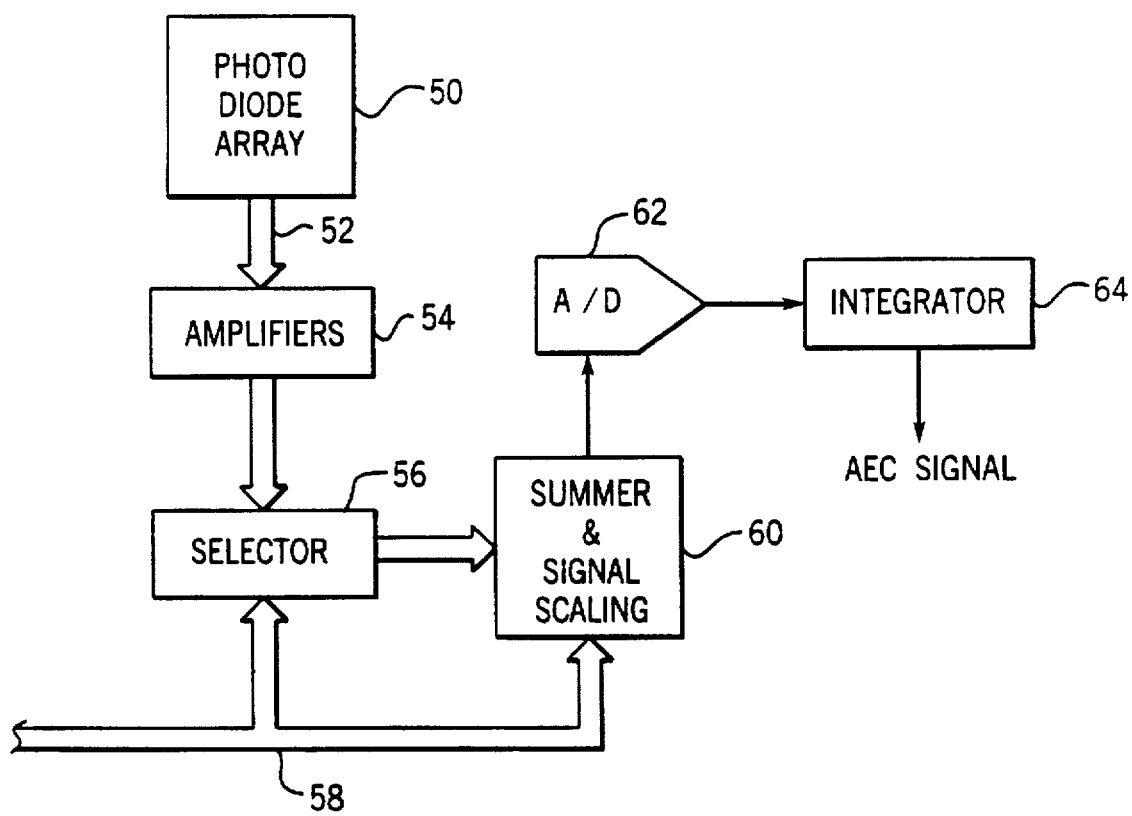
FIG. 3 is a block diagram of the preferred embodiment of the AEC photosensor array of the present invention.

Referring particularly to FIG. 3, in a preferred embodiment the AEC photosensor array 23 is a photodiode array 50. The photodiode array 50 is disposed behind the imaging detector from which the exposure is to be monitored for the purpose of exposure control. Light which impinges on the surface of the photodiode array 50 creates electron-hole pairs in the photodiodes it strikes, and this produces a current when connected to an external circuit. The signal created from the array 50 is used for automatic exposure control.

Figure 4:
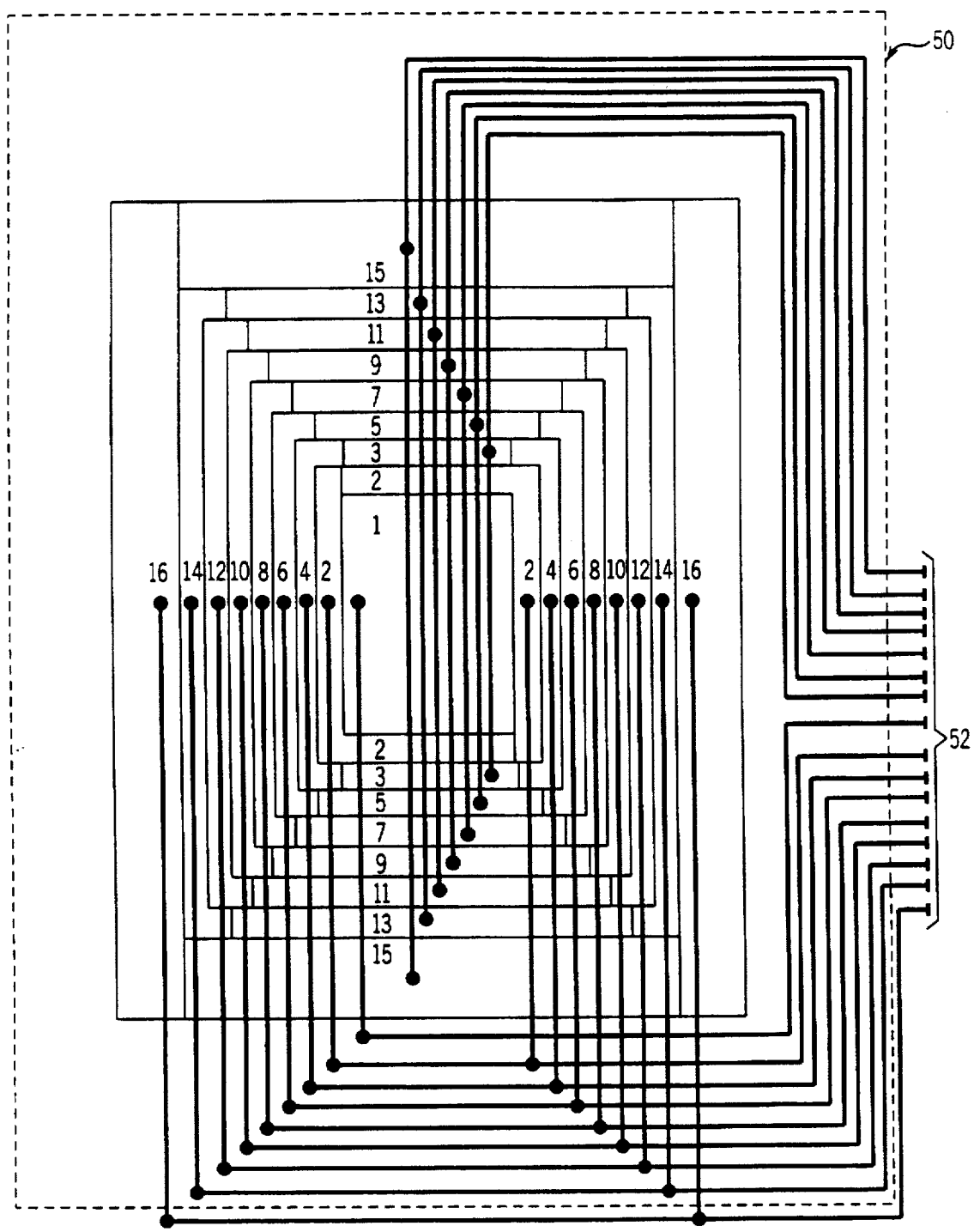
FIG. 4 is a schematic representation of a first embodiment of a photodiode array which forms part of the AEC photosensor array of FIG. 3.
Figure 5:
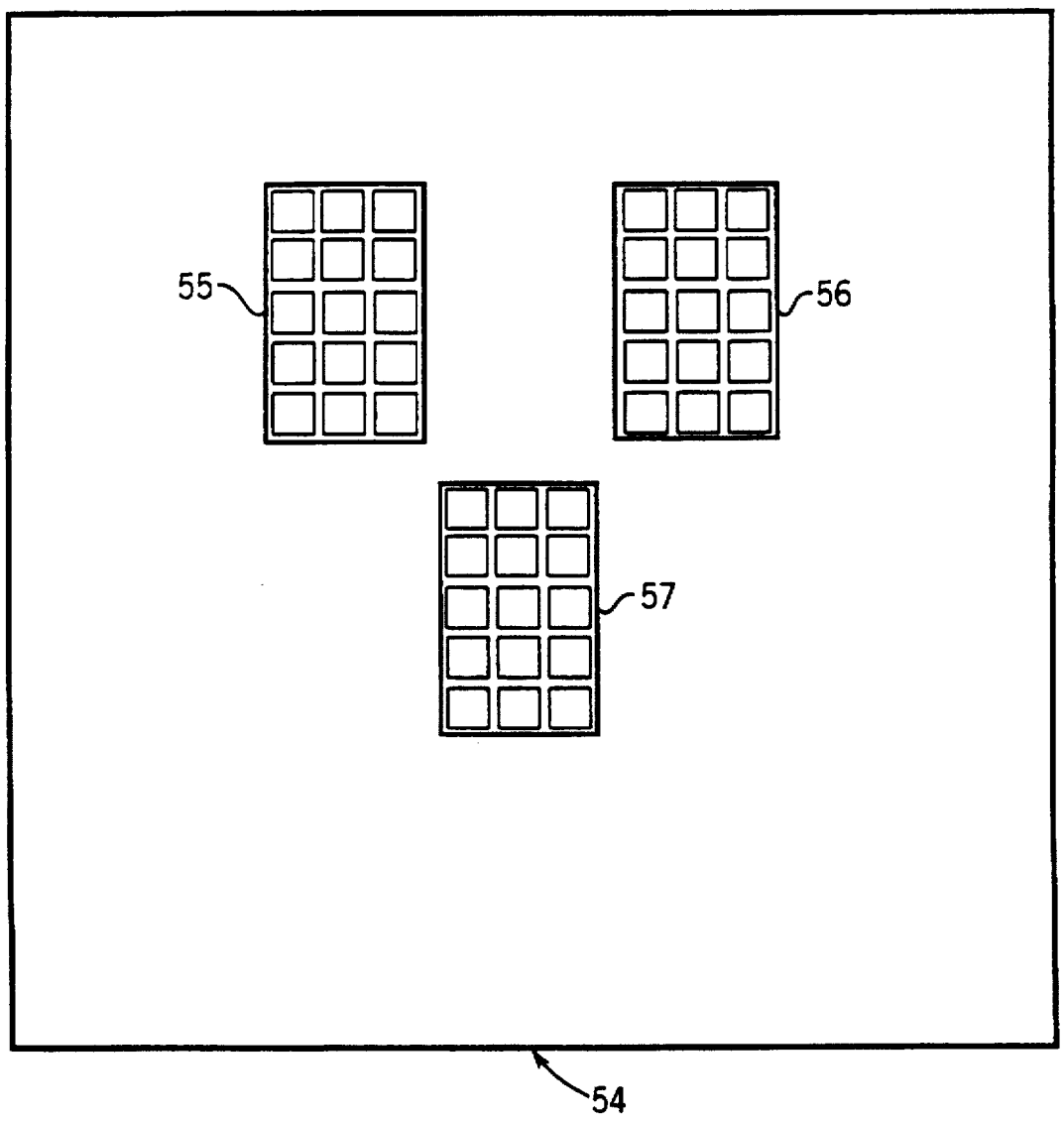
FIG. 5 is an alternative embodiment of the photodiode array employed in the AEC photosensor array of FIG. 3.

The arrangement of the elements in the array 50 is designed to enable x-ray intensity to be monitored for specific anatomical areas as may be required by the particular examination being performed as well as the size of the field of view. A preferred embodiment of the photodiode array 50 is shown in FIG. 4. The photodiodes in the array 50 are assembled into regions designated 1–16. All of the photodiodes in each region have their outputs connected together to provide a regional signal. One of sixteen output leads 52 connects to each region to bring out the regional signal from the photodiodes therein. It should be apparent from FIG. 4, that by selectively combining the regional signals on the sixteen leads 52, the size and shape of the area from which the AEC signals are gathered can be changed. Region 1 occupies a central, square area, and the remaining regions 2–16 enable the size and shape of this central area to be expanded outward. By selectively combining the regional signals on the leads 52, therefore, the size and shape of the area monitored by the AEC photosensor array 23 can be adjusted as required for specific patient examination. The AEC photodiode array 50 in FIG. 4 is used with a 20 cm by 20 cm imaging detector. The size of the array and the location and grouping of the diodes will be different for other imaging detectors. In particular, some detectors require the diodes to be grouped into disconnected areas, possibly of different sizes and shapes. FIG. 5 shows an example of such an AEC photodiode array 54 which includes three separate sense areas 55, 56 and 57. This grouping of diodes mimics the geometry of the particular ion chamber AEC detector used with 35 by 43 centimeter film/screen imaging detectors.

Referring again to FIG. 3, the signals on leads 52 are separately amplified at 54. The signal from each region is proportional to the exposure in that region times the area of the region. If the control signal is desired to contain equal weighting from throughout the control area, the gain of each amplifier is adjusted to be inversely proportional to the area of its region. Alternatively, if the weighting of some parts of the control area is desired to be greater than other parts, the gains can be appropriately adjusted. The sixteen amplified signals are then applied to a selector 56 which receives a selection control signal 58 that indicates which ones of the amplified signals are to be combined to form the composite AEC signal. The selector 56 is comprised of analog switches. The selection control signal is determined by the selected field of view of the image and the type of patient examination selected by the operator and it is produced by the system controller 36 (FIG. 1). The selected signals are applied to a summing and signal scaling amplifier 60 which combines them and then scales the resulting composite AEC signal in inverse proportion to the number of regions selected. While this composite analog AEC signal may be integrated and used to control x-ray exposure directly, in the preferred embodiment the composite AEC signal is digitized by an analog-to-digital converter 62. The digitized composite AEC signal is integrated as shown at 64 and used to control exposure as described above.

Those skilled in the art will appreciate that many variations are possible from the above described embodiments of the invention without departing from the spirit of the invention. For example, the circuit of FIG. 3 can be modified to digitize the analog signals from each region prior to being combined. This enables the weighting and combining functions to be performed digitally.

We claim:

1. In an x-ray system the improvement comprising:
   a large area solid state image detector;
   an array of photosensors disposed behind the image detector and positioned to detect photons passing through the image detector;
   means for combining currents produced by photosensors in said array;
   an integrator connected to the means for combining for providing an AEC signal; and
   an exposure control connected to receive the AEC signal and employ the same to control x-ray exposure.

2. The improvement as recited in claim 1 in which the means for combining includes a selector that selects photosensor currents to be combined.

3. The improvement as recited in claim 2 which includes a system controller that operates said selector to determine the area over which the AEC signal is to be acquired.

4. The improvement as recited in claim 1 in which the means for combining includes means for scaling the AEC signal based on the number of photosensor currents combined.

5. The improvement as recited in claim 1 in which photosensors in each of a plurality of regions in the array are connected together such that their currents are summed together to form regional signals.

6. The improvement as recited in claim 5 in which the means for combining includes a selector that selects regional signals to be combined in response to a selection control signal.

* * * * *